US009301737B2

(12) United States Patent
Leimbach et al.

(10) Patent No.: US 9,301,737 B2
(45) Date of Patent: Apr. 5, 2016

(54) NEEDLE TIP FOR BIOPSY DEVICE (71) Applicant: Devicor Medical Products, Inc., Cincinnati, OH (US)

(72) Inventors: Jessica P. Leimbach, Cincinnati, OH (US); Edward A. Rhad, Fairfield, OH (US)

(73) Assignee: DEVICOR MEDICAL PRODUCTS INC., Cincinnati, OH (US)

( * ) Notice: Subject to any disclaimer, the term of this patent is extended or adjusted under 35 U.S.C. 154(b) by 196 days.

(21) Appl. No.: 14/101,805

(22) Filed: Dec. 10, 2013

(65) Prior Publication Data

US 2014/0094714 A1 Apr. 3, 2014

Related U.S. Application Data (63) Continuation of application No. 12/711,310, filed on Feb. 24, 2010, now Pat. No. 8,628,482.

(51) Int. Cl.
*A61B 5/00* (2006.01)
*A61B 10/02* (2006.01)

(52) U.S. Cl.
CPC ......... *A61B 10/0275* (2013.01); *A61B 10/0283* (2013.01); *A61B 2010/0208* (2013.01)

(58) Field of Classification Search
CPC ............... A61B 10/02; A61B 10/0233; A61B 10/0266; A61B 10/0275
See application file for complete search history.

(56) References Cited

U.S. PATENT DOCUMENTS

| | | | |
|---|---|---|---|
| 5,526,822 A | 6/1996 | Burbank et al. | |
| 5,823,970 A | 10/1998 | Terwilliger | |
| 6,086,544 A | 7/2000 | Hibner et al. | |
| 6,626,849 B2 | 9/2003 | Huitema et al. | |
| 7,442,171 B2 | 10/2008 | Stephens et al. | |
| 7,854,706 B2 | 12/2010 | Hibner | |
| 7,895,725 B2 * | 3/2011 | Beckman et al. | ............... 29/458 |
| 7,918,804 B2 | 4/2011 | Monson et al. | |
| 7,951,089 B2 | 5/2011 | Miller | |
| 8,002,713 B2 * | 8/2011 | Heske et al. | .................. 600/566 |
| 8,206,316 B2 | 6/2012 | Hibner et al. | |
| 8,622,924 B2 | 1/2014 | Speeg et al. | |
| 8,668,698 B2 | 3/2014 | Miller et al. | |
| 2006/0074345 A1 | 4/2006 | Hibner | |
| 2006/0074443 A1 | 4/2006 | Foerster et al. | |
| 2008/0214955 A1 | 9/2008 | Speeg et al. | |
| 2010/0152610 A1 | 6/2010 | Parihar et al. | |
| 2010/0160819 A1 | 6/2010 | Parihar et al. | |

\* cited by examiner

*Primary Examiner* — Max Hindenburg
(74) *Attorney, Agent, or Firm* — Frost Brown Todd LLC (57) ABSTRACT

A biopsy device includes a body portion, a cannula, a cutter, and a tissue stop having a proximal face. The cannula has a transverse aperture that is defined in part by a proximal edge and a distal edge. The cutter is movable to a distal position to sever tissue protruding through the transverse aperture. A tip at the distal end of the cannula has a sharp edge that extends proximally to a longitudinal position that is proximal to the longitudinal position of the distal edge of the transverse aperture. The sharp edge of the tip extends to a longitudinal position that is proximal to the longitudinal position of the distal cutting edge of the cutter when the cutter is at the distal position. The sharp edge of the tip extends to a longitudinal position that is proximal to the longitudinal position of the proximal face of the tissue stop.

19 Claims, 6 Drawing Sheets

NEEDLE TIP FOR BIOPSY DEVICE

BACKGROUND

Biopsy samples have been obtained in a variety of ways in various medical procedures using a variety of devices. Biopsy devices may be used under stereotactic guidance, ultrasound guidance, MRI guidance, PEM guidance, BSGI guidance, or otherwise. For instance, some biopsy devices may be fully operable by a user using a single hand, and with a single insertion, to capture one or more biopsy samples from a patient. In addition, some biopsy devices may be tethered to a vacuum module and/or control module, such as for communication of fluids (e.g., pressurized air, saline, atmospheric air, vacuum, etc.), for communication of power, and/or for communication of commands and the like. Other biopsy devices may be fully or at least partially operable without being tethered or otherwise connected with another device.

Merely exemplary biopsy devices are disclosed in U.S. Pat. No. 5,526,822, entitled "Method and Apparatus for Automated Biopsy and Collection of Soft Tissue," issued Jun. 18, 1996; U.S. Pat. No. 6,086,544, entitled "Control Apparatus for an Automated Surgical Biopsy Device," issued Jul. 11, 2000; U.S. Pub. No. 2003/0109803, entitled "MRI Compatible Surgical Biopsy Device," published Jun. 12, 2003; U.S. Pub. No. 2006/0074345, entitled "Biopsy Apparatus and Method," published Apr. 6, 2006; U.S. Pub. No. 2007/0118048, entitled "Remote Thumbwheel for a Surgical Biopsy Device," published May 24, 2007; U.S. Pub. No. 2008/0214955, entitled "Presentation of Biopsy Sample by Biopsy Device," published Sep. 4, 2008; U.S. Pub. No. 2009/0171242, entitled "Clutch and Valving System for Tetherless Biopsy Device," published Jul. 2, 2009; U.S. patent application Ser. No. 12/335,578, entitled "Hand Actuated Tetherless Biopsy Device with Pistol Grip," filed Dec. 16, 2008; U.S. patent application Ser. No. 12/337,942, entitled "Biopsy Device with Central Thumbwheel," filed Dec. 18, 2008; and U.S. patent application Ser. No. 12/483,305, entitled "Tetherless Biopsy Device with Reusable Portion," filed Jun. 12, 2009. The disclosure of each of the above-cited U.S. Patents, U.S. Patent Application Publications, and U.S. Patent Applications is incorporated by reference herein.

In some settings, including some of those where a biopsy device tip needs to penetrate the tissue of a patient, some users of biopsy devices may prefer that the tip penetrate tissue with relatively little force. In other words, in some settings, a user may prefer a first biopsy device over a second biopsy device due to the first biopsy device requiring less force for its tip to penetrate tissue than the force required for the tip of the second biopsy device to penetrate tissue. This preference may be heightened when the tissue is relatively dense or under other circumstances. This preference may also be present in settings where the biopsy device tip is inserted in tissue by hand (e.g., rather than using a firing mechanism, etc.).

Some biopsy devices may have a needle portion that has a generally circular cross-section, a generally ovular cross-section, a generally elliptical cross-section, a "figure eight" type of cross section, or some other cross-section. Such needle portions may have a predefined outer perimeter about a longitudinal axis. In some settings, the ratio of the length of an incision in tissue to the length of the perimeter or circumference of a biopsy device needle may be indicative of the magnitude of the force required to push the needle into dense tissue. For instance, in some settings, a relatively higher ratio of incision length to outer perimeter length may yield rises in tissue dilation hoop stresses that are more ideal (e.g., lower rates of rise) than rises in tissue dilation hoop stresses obtained using a relatively lower ratio of incision length to outer perimeter length (e.g., higher rates of rise).

While several systems and methods have been made and used for obtaining a biopsy sample, it is believed that no one prior to the inventors has made or used the invention described in the appended claims.

BRIEF DESCRIPTION OF THE DRAWINGS

While the specification concludes with claims which particularly point out and distinctly claim the invention, it is believed the present invention will be better understood from the following description of certain examples taken in conjunction with the accompanying drawings, in which like reference numerals identify the same elements and in which:

DETAILED DESCRIPTION

The following description of certain examples of the invention should not be used to limit the scope of the present invention. Other examples, features, aspects, embodiments, and advantages of the invention will become apparent to those skilled in the art from the following description, which is by way of illustration, one of the best modes contemplated for carrying out the invention. As will be realized, the invention is capable of other different and obvious aspects, all without departing from the invention. Accordingly, the drawings and descriptions should be regarded as illustrative in nature and not restrictive.

Figure 1:
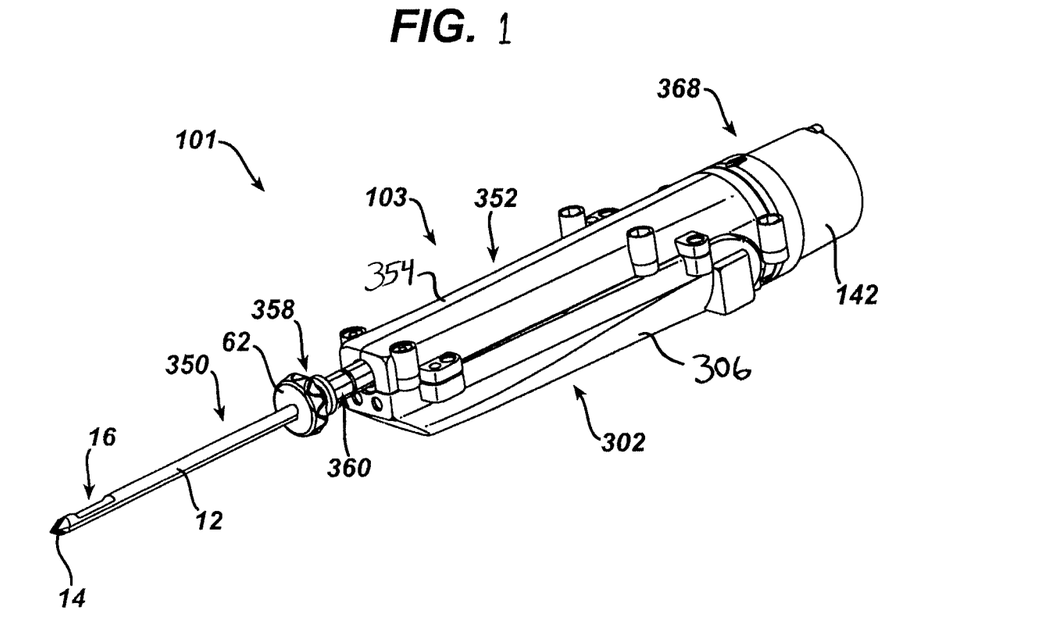
FIG. 1 depicts a perspective view of an exemplary assembled biopsy device, for use in an ultrasound setting.
Figure 2:
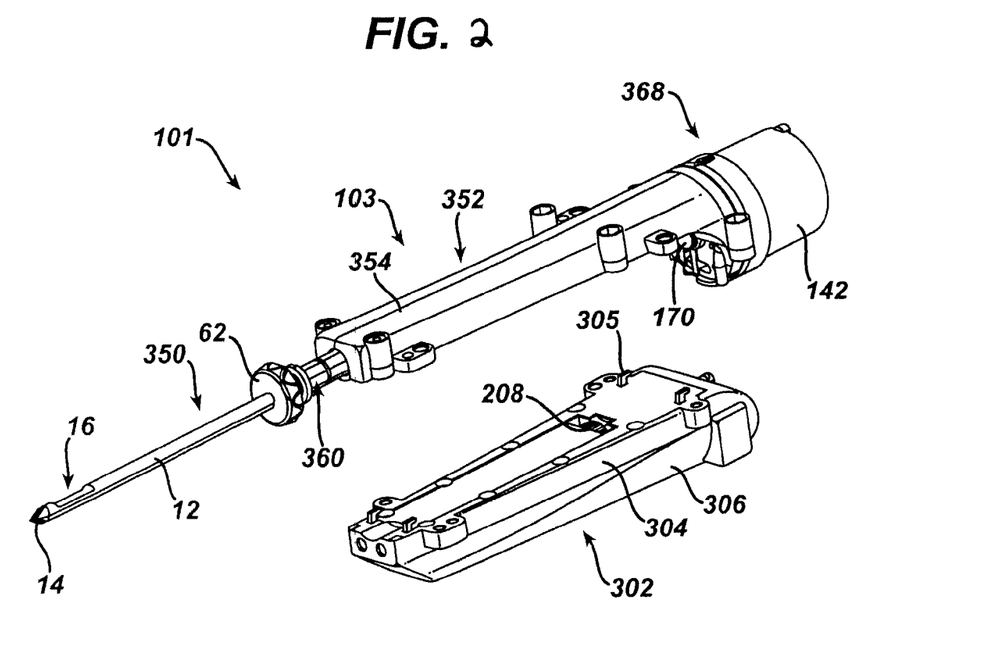
FIG. 2 depicts an exploded view of the biopsy device of FIG. 1, with the probe detached from the holster.

As shown in FIGS. 1-2, an exemplary biopsy device (101) comprises a probe (103) and a holster (302). Probe (103) is separable from holster (302). By way of example only, probe (103) may be provided as a disposable component, while holster (302) may be provided as a reusable component. Use of the term "holster" herein should not be read as requiring any portion of probe (103) to be inserted into any portion of holster (302). Indeed, in some variations of biopsy device (101), probe (103) may simply sit on holster (302). In some other variations, a portion of holster (302) may be inserted into probe (103). Furthermore, in some biopsy devices (101), probe (103) and holster (302) may be of unitary or integral construction, such that the two components cannot be separated or are not identifiable as different components. Still other suitable structural and functional relationships between probe (103) and holster (302) will be apparent to those of ordinary skill in the art in view of the teachings herein.

I. Exemplary Probe

Figure 3:
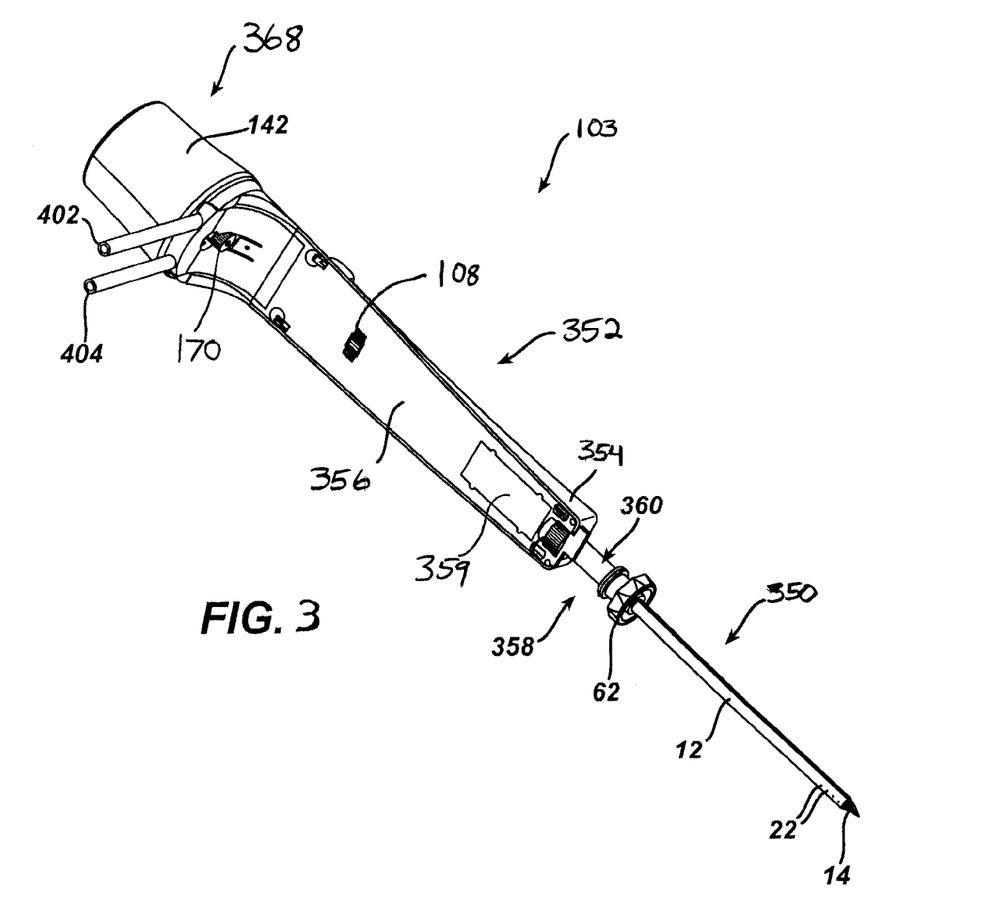
FIG. 3 depicts a bottom perspective view of the probe portion of FIG. 2.

As shown in FIGS. 1-3, biopsy probe (103) of the present example comprises a needle portion (350) and a body portion (352). Body portion (352) comprises a cover member (354) and a base member (356). A tissue sample holder (368) is removably secured to base member (356), though tissue sample holder (368) may alternatively be secured to cover member (354) or some other component. A pair of tubes (402, 404) are coupled with probe (103). As will also be described in greater detail below, and as noted above, biopsy probe (103) is configured to be coupled with a holster (302) to provide a biopsy device (101).

A. Exemplary Needle

Figure 4:
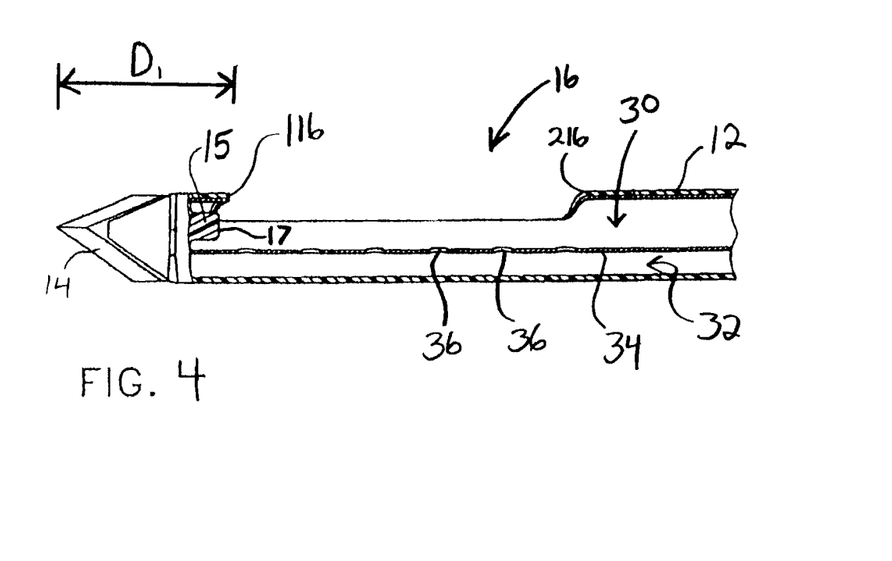
FIG. 4 depicts a partial side view of the distal end of the needle of the biopsy device of FIG. 1, with the needle shown in cross section.
Figure 5:
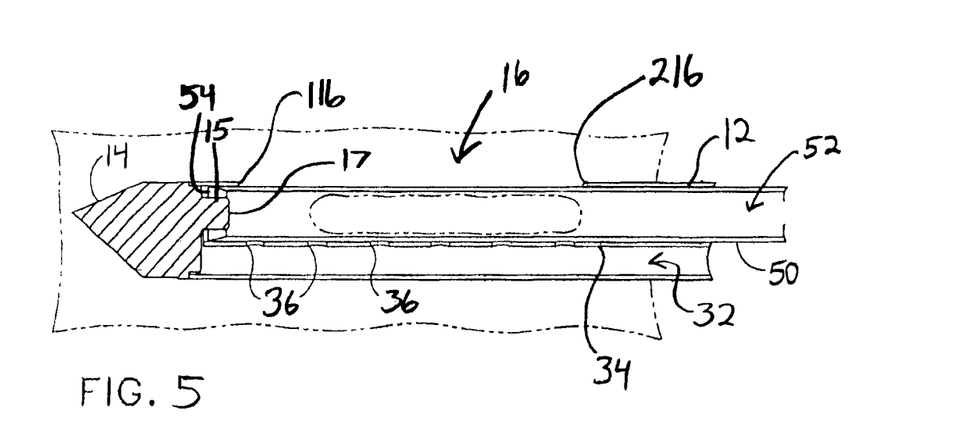
FIG. 5 depicts a partial side view of the distal end of the needle of the biopsy device of FIG. 1, with the needle and cutter shown in cross section, and with the cutter advanced to a distal position.

In the present example, needle portion (350) comprises an outer cannula (12) having a tissue piercing tip (14) and a transverse tissue receiving aperture (16) located proximally from the tissue piercing tip (14). Transverse aperture (16) is defined in part by a distal edge (116) and a proximal edge (216). As shown in FIGS. 4-5, the interior of outer cannula (12) of the present example defines a cannula lumen (30) and a vacuum lumen (32), with a wall (34) separating cannula lumen (30) from vacuum lumen (32). Transverse aperture (16) opens into cannula lumen (30), such that tissue may be received in cannula lumen (30) via transverse aperture (16). Wall (34) between cannula lumen (30) and vacuum lumen (32) has a plurality of openings (36), permitting fluid communication between cannula lumen (30) and vacuum lumen (32). In some versions, wall (34) extends proximally along a substantial part of the full length of outer cannula (12), if not the full length of outer cannula (12). In some other versions, wall (34) extends proximally along just a part of the length of outer cannula (12). For instance, wall (34) may extend proximally along part of the length of outer cannula (12), terminating at a longitudinal position that is passed through by a transverse plane that is just proximal to a transverse plane passing through proximal edge (216) of transverse aperture (16). Thus, in some such versions, wall (34) and the inner surface of outer cannula (12) together define a first part of vacuum lumen (32); while the outer surface of cutter (50) and the inner surface of outer cannula (12) together define a second part of vacuum lumen (32). In some such versions, cannula lumen (30) may be viewed as terminating at the same longitudinal positions at which wall (34) terminates.

A tissue stop (15), which has a generally cylindraceous shape in this example, extends proximally in cannula lumen (30). As shown in FIG. 3, a plurality of external openings (22) are formed in outer cannula (12), and are also in fluid communication with vacuum lumen (32). Such external openings (22) may be configured an operable in accordance with any of the teachings of U.S. Pub. No. 2007/0032742, entitled "Biopsy Device with Vacuum Assisted Bleeding Control," published Feb. 8, 2007, the disclosure of which is incorporated by reference herein. Of course, as with other components described herein, external openings (22) are merely optional. Various other suitable components, features, and configurations that needle portion (350) may have will be apparent to those of ordinary skill in the art.

B. Exemplary Cutter

A hollow cutter (50) is slidably disposed within cannula lumen (30) of cannula (12). The interior of cutter (50) defines a cutter lumen (52), such that fluid and tissue may be communicated through cutter (50) via cutter lumen (52). Cutter (50) is configured to rotate within cannula lumen (30) and translate axially within cannula lumen (30). Such simultaneous rotation and translation of cutter (50) is accomplished by rotating gear (108), which meshes with corresponding gear (208) of holster (302). Suitable mechanisms that may be provided for causing cutter (50) to simultaneously rotate and translate are disclosed in U.S. Pub. No. 2008/0214955, entitled "Presentation of Biopsy Sample by Biopsy Device," published Sep. 4, 2008, the disclosure of which is incorporated by reference herein; while other suitable mechanisms will be apparent to those of ordinary skill in the art in view of the teachings herein.

Cutter (50) has a sharpened distal end (54) that is configured to sever a biopsy sample from tissue protruding through transverse aperture (16) of outer cannula (12). In particular, cutter (50) is configured to sever tissue protruding through transverse aperture as cutter (50) translates to a distal-most position, where distal end (54) of cutter (50) is located distal to distal edge (116) transverse aperture (16). In the present example, cutter (50) also rotates during such distal translation. Cutter (50) is further configured to permit severed tissue samples to be communicated proximally through cutter lumen (52). Merely illustrative examples of such severing and proximal communication are described in U.S. Pat. No. 5,526,822, the disclosure of which is incorporated by reference herein, though any other suitable structures or techniques may be used for severing and/or communicating tissue samples. As shown in FIG. 5, cutter lumen (52) is configured to receive part of tissue stop (15) when cutter (50) is at a distal-most position. In particular, distal end (54) of cutter (54) travels distally past the proximal face (17) of tissue stop (15). Tissue stop (15) is thus configured to assist in "stuffing" a severed tissue sample proximally into cutter lumen (52) as cutter (50) reaches the distal-most position. The severed tissue sample may then be drawn proximally through cutter lumen (52) to reach tissue sample holder (368) under the assistance of a vacuum and/or a pressurized medium as described in the various patent references cited herein.

Other suitable components of, structures for, relationships between, and configurations for cannula (20) and cutter (50) are disclosed in U.S. Pub. No. 2008/0214955, entitled "Presentation of Biopsy Sample by Biopsy Device," published Sep. 4, 2008, the disclosure of which is incorporated by reference herein. Of course, any other suitable components, structures, or configurations may be used.

C. Exemplary Tissue Piercing Tips

Tissue piercing tip (14) of the present example is configured to penetrate tissue without requiring a high amount of force, and without requiring an opening to be preformed in the tissue prior to insertion of tip (14). Of course, in some versions of use, an incision or other opening may be formed in the tissue prior to insertion of tip (14). While a variety of merely exemplary tips (14) will be described in greater detail below, it should be understood that a variety of other tips (14) may be used. In some versions, a tip (14) may provide penetration in fibrous breast tissue with as little as approximately 20 newtons or approximately 4 pounds of force, if not less force, through and past a depth of at least 6 mm into the tissue. For instance, some versions of various tips (14) described herein may require less than approximately 20 newtons or less than approximately 4 pounds of force to penetrate through 10 mm, 20 mm, 30 mm, 40 mm, 50 mm, 60 mm, and/or greater depths of breast tissue. In other words, a tip (14) may penetrate through to any or all such depths without ever requiring an insertion force that exceeds approximately 20 newtons or approximately 4 pounds of force during such penetration. Some versions of various tips (14) described herein may even require less than approximately 15 newtons or less than approximately 3 pounds of force to penetrate through 10 mm, 20 mm, 30 mm, 40 mm, 50 mm, 60 mm, and/or greater depths of breast tissue. Alternatively, tips (14) may require any other suitable force to penetrate tissue to any desired depth. In other words, the above-noted forces of less than approximately 20 newtons or less than approximately 4 pounds of force to penetrate are merely illustrative, non-limiting examples.

It should be understood that the design of a cannula (12) and tip (14) may provide a certain amount of "dead space" that affects the depth to which cannula (12) may be inserted in tissue. Such a dead space may be defined as the length of needle portion (350) that extends distally past distal edge (116) of transverse aperture (16). In FIG. 4, this dead space is shown as the distance "$D_1$." This dead space length may pose difficulties when a user is attempting to acquire tissue samples from a relatively small breast. For instance, cannula (12) may need to be inserted into the breast to a depth sufficient to locate a targeted lesion adjacent to transverse aperture (16), and hence, proximal to distal edge (116) of transverse aperture (16). However, inserting the cannula (12) to such a depth in a relatively small breast may present a risk of tip (14) piercing the pectoralis major muscle, piercing intercostal muscles, striking a rib, and/or other piercing or otherwise striking anatomical structures behind the breast. Alternatively, depending on the angle of insertion, inserting the cannula (12) to such a depth in a relatively small breast may present a risk of tip (14) piercing through the skin of the breast opposite to the cannula (12) insertion site. To the extent that it is desirable to avoid these risks, cannula (12) and/or tip (14) may be designed to reduce the length of dead space, thereby reducing the risks associated with an otherwise relatively long dead space at the distal end of needle portion (350). In some settings, it may be desirable that such designs do not significantly increase the amount of force required to penetrate tissue with tip (14) and cannula (12). In other words, it may be desirable in some settings to provide a needle portion (350) with a dead space length sufficient to allow biopsy device (101) to be used with a relatively small breast while also requiring only a relatively low force to penetrate the breast with tip (14) and cannula (12).

Figure 6:
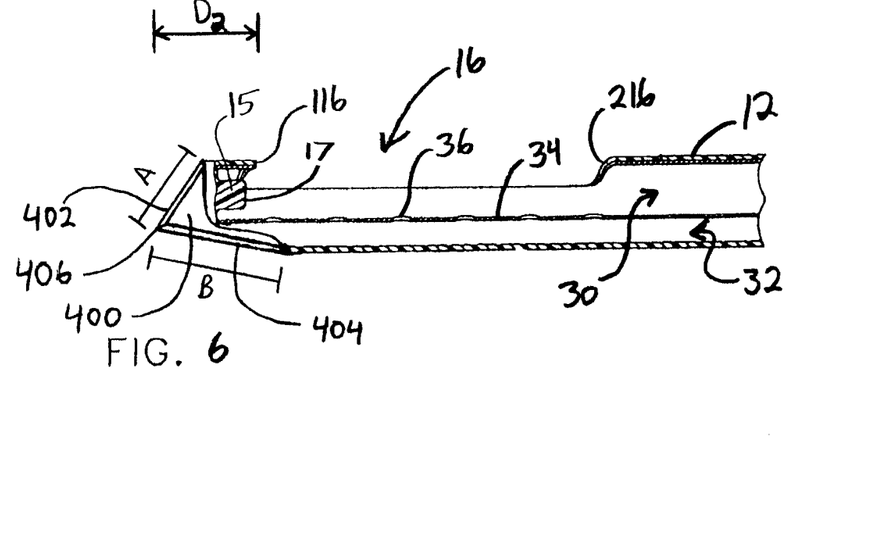
FIG. 6 depicts a partial side view of the distal end of the needle of the biopsy device of FIG. 1, with the needle shown in cross section, and with an exemplary alternative needle tip.
Figure 7:
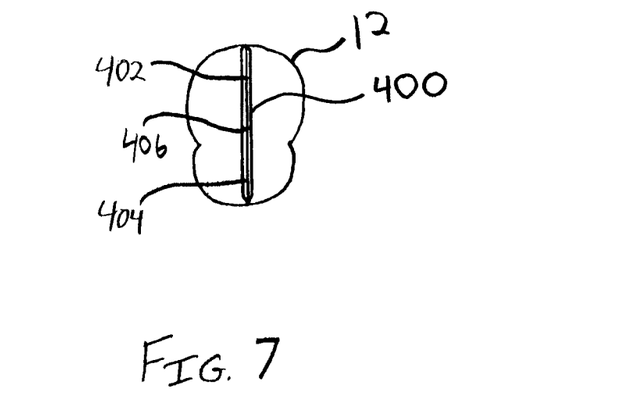
FIG. 7 depicts an end view of the modified needle of FIG. 6.

FIGS. 6-7 depict a merely exemplary needle tip (400) that may be provided on a needle portion (350), providing a relatively short dead space. In FIG. 6, this dead space is shown as the distance "$D_2$." Needle tip (400) of this example is formed as a blade having an upper sharpened edge (402) and a lower sharpened edge (404), which converge together at a sharp point (406). Edges (402, 404) define an acute angle at point (406). Alternatively, edges (402, 404) may define any other suitable angle.

In FIG. 6, the length of upper edge (402) is shown as the distance "A"; while the length of lower edge (404) is shown as the distance "B". In the present example, the sum of lengths "A" and "B" provides an incision length (not shown) as tip (400) is inserted into tissue. The ratio of this incision length to the length of the outer perimeter of cannula (12) about the longitudinal axis of cannula (12) is relatively higher than the corresponding ratio provided by tip (14) of FIGS. 4-5. Thus, a cannula (12) having tip (400) may require less force to penetrate tissue than the force that would be required to penetrate tissue with a cannula (12) having tip (14). Furthermore, since the dead space "$D_2$" of cannula (12) having tip (400) is less than the dead space "$D_1$" of cannula (12) having tip (14), it may be easier to acquire tissue samples with cannula (12) having tip (400) in a relatively small breast.

As shown in FIG. 6, the combination of reduced dead space and relatively high ratio of incision length to cannula (12) perimeter length is accomplished in part by having lower edge (404) extend proximally to a degree that is greater than the proximal extent to which tip (14) extends. In particular, lower edge (404) extends proximally to a longitudinal position that is proximal to proximal face (17) of tissue stop (15) and that is also proximal to distal edge (116) of transverse aperture (16). In comparing FIG. 4 with FIG. 6, it can be seen that this configuration of lower edge (404) reduces the length to which vacuum lumen (32) extends distally. In other words, the design of tip (400) in this example utilizes space that might otherwise constitute dead space in vacuum lumen (32). In the present example, such utilization of otherwise dead space in vacuum lumen (32) does not adversely affect performance of biopsy device (101) in any way.

As shown in FIG. 7, cannula (12) of the present example has a cross section resembling a figure eight, with the region corresponding with cannula lumen (30) being relatively larger than the region corresponding with vacuum lumen (32). The perimeter length of cannula (12) extends along this figure eight profile, about the longitudinal axis of cannula (12). Tip (400) of the present example is configured such that cut length produced by tip (400) is greater than or equal to the perimeter length or circumference of cannula (12). It will be appreciated, however, that any other suitable dimensions or relationships between cannula (12) and tip (400) dimensions may be used. It should also be understood that cannula (12) may have any other suitable cross section or profile shape, including but not limited to circular, ovular, elliptical, etc.

As noted above and as can be seen in FIGS. 6-7, tip (400) of the present example is formed as a substantially flat blade extending distally from cannula (12). It should be understood, however, that tip (400) may have a variety of other configurations. For instance, tip (400) may have a pyramidal configuration with three sides, four sides, or any other suitable number of sides, with sharp edges at the junction of adjacent sides. One or more of such sharp edges may extend proximally past distal face (17) of tissue stop (15) and/or past distal edge (116) of transverse aperture (16), similar to lower edge (404) shown in FIG. 6. As another merely illustrative alternative, tip (400) may include one or more additional blades. For instance, an additional blade may extend perpendicular (e.g., horizontal) to the blade shown in FIGS. 6-7. Other suitable variations of tip (400) will be apparent to those of ordinary skill in the art in view of the teachings herein. In some versions, tip (400) is integral and unitary with cannula (12), such that tip (400) is formed as an integral and unitary portion of cannula (12). In still other versions, tip (400) and cannula (12) are formed separately then joined together. In such versions, tip (400) may formed before tip (400) is secured to cannula (12). Alternatively, tip (400) may be formed after tip (400) is secured to cannula (12). Of course, tip (400) and cannula (12) may be formed in any other suitable fashion and may have any other suitable relationships.

Figure 8:
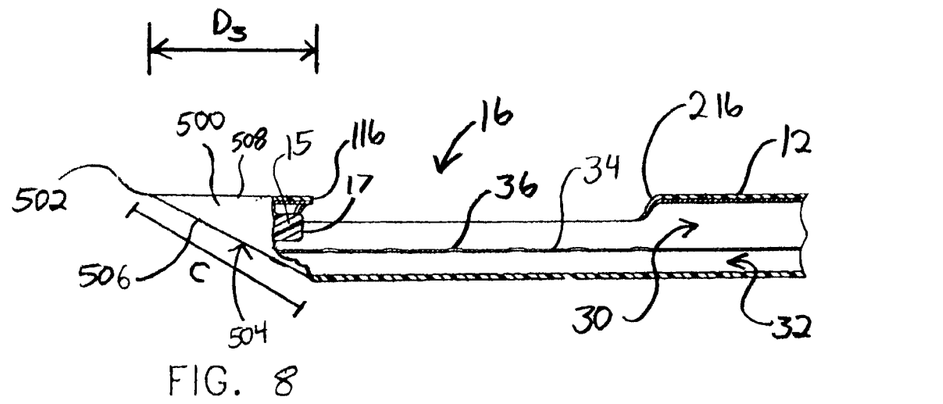
FIG. 8 a partial side view of the distal end of the needle of the biopsy device of FIG. 1, with the needle shown in cross section, and with another exemplary alternative needle tip.
Figure 9:
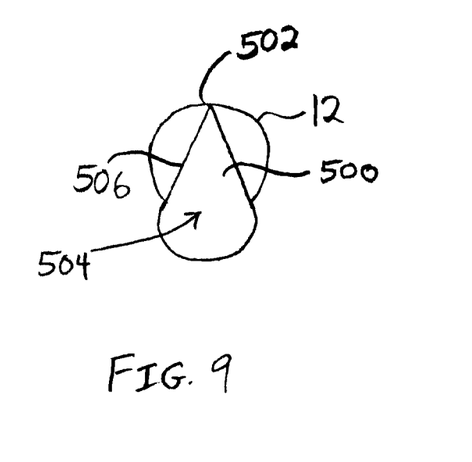
FIG. 9 depicts an end view of the modified needle of FIG. 8.

FIGS. 8-9 depict another merely exemplary needle tip (500) that may be provided on a needle portion (350), providing a relatively short dead space. In FIG. 8, this dead space is shown as the distance "$D_3$." Needle tip (500) of this example is configured like a hypodermic needle tip, albeit with no central bore being formed through needle tip (500). In particular, needle tip (500) terminates distally in a sharp point (502) and presents an angled distal face (504). As shown in FIG. 9, distal face (504) has a teardrop shape defined by a sharp outer edge (506) in this example. The top edge (508) of tip (500) is substantially parallel to the longitudinal axis of cannula (12), and defines an acute angle with outer edge (506) as shown in FIG. 8. Alternatively, edges (506, 508) may define any other suitable angle.

In FIG. 8, the length of outer edge (506) is shown as the distance "C." In the present example, the length "C" provides an incision length (not shown) as tip (500) is inserted into tissue. The ratio of this incision length to the length of the outer perimeter of cannula (12) about the longitudinal axis of cannula (12) is relatively higher than the corresponding ratio provided by tip (14) of FIGS. 4-5. Thus, a cannula (12) having tip (500) may require less force to penetrate tissue than the force that would be required to penetrate tissue with a cannula (12) having tip (14). Furthermore, since the dead space "D3" of cannula (12) having tip (500) is less than the dead space "$D_1$" of cannula (12) having tip (14), it may be easier to acquire tissue samples with cannula (12) having tip (500) in a relatively small breast.

As shown in FIG. 8, the combination of reduced dead space and relatively high ratio of incision length to cannula (12) perimeter length is again accomplished in part by having outer edge (506) extend proximally to a degree that is greater than the proximal extent to which tip (14) extends. In particular, outer edge (506) extends proximally to a longitudinal position that is proximal to proximal face (17) of tissue stop (15) and that is also proximal to distal edge (116) of transverse aperture (16). In comparing FIG. 4 with FIG. 8, it can be seen that this configuration of outer edge (506) reduces the length to which vacuum lumen (32) extends distally. In other words, the design of tip (500) in this example utilizes space that might otherwise constitute dead space in vacuum lumen (32). In the present example, as with tip (400) shown in FIGS. 6-7, such utilization of otherwise dead space in vacuum lumen (32) does not adversely affect performance of biopsy device (101) in any way.

As with tip (400) shown in FIGS. 6-7, tip (500) of the present example is configured such that cut length produced by tip (500) is greater than or equal to the perimeter length or circumference of cannula (12). It will be appreciated, however, that any other suitable dimensions or relationships between cannula (12) and tip (500) dimensions may be used. It should also be understood that cannula (12) may have any other suitable cross section or profile shape, including but not limited to circular, ovular, elliptical, etc. Other suitable variations of tip (500) will be apparent to those of ordinary skill in the art in view of the teachings herein. In some versions, tip (500) is integral and unitary with cannula (12), such that tip (500) is formed as an integral and unitary portion of cannula (12). In still other versions, tip (500) and cannula (12) are formed separately then joined together. In such versions, tip (500) may formed before tip (500) is secured to cannula (12). Alternatively, tip (500) may be formed after tip (500) is secured to cannula (12). Of course, tip (500) and cannula (12) may be formed in any other suitable fashion and may have any other suitable relationships.

The above described variations (400, 500) of tip are mere examples. Other suitable configurations for a tissue piercing tip (14) or other components of needle portion (350) will be apparent to those of ordinary skill in the art in view of the teachings herein.

D. Exemplary Cannula Modifications

In addition to or in lieu of providing any of the various versions of tip (14) described herein, cannula (12) may be subject to various modifications. Such modifications may reduce the force that is required for needle portion (350) to penetrate into tissue. One such modification may include applying a carbon or hydrophilic coating to the outer surface of cannula (12) and/or tip (14). Alternatively, any other coating or treatment may be applied to cannula (12) and/or tip (14). In some versions, cannula (12) is subject to shot peening, which results in a plurality of dimples being formed in cannula (12). It will be appreciated that, in some contexts, a cannula (12) that has a smooth electropolished outside surface may exhibit some degree of adherence to tissue as it penetrates the tissue. Such adherence may result in a relatively increased force that is required for a needle portion (350) that has such a cannula (12) to penetrate the tissue. By contrast, dimples in cannula (12) may reduce such a drag effect (e.g., by reducing the contact surface), such that a modified cannula requires relatively less force for needle portion (10) to penetrate tissue. Dimples may be provided along any suitable length of cannula (350). As another merely illustrative example, cannula (350) may have a plurality of scallops formed therein, a plurality of longitudinal grooves formed therein, and/or various other structural features that reduce the force required to penetrate tissue with cannula (12). Various suitable ways in which the above-described modifications of cannula (350) may be carried are described in U.S. Pub. No. 2009/0216152, entitled "Needle Tip for Biopsy Device," published Aug. 27, 2009, the disclosure of which is incorporated by reference herein.

The above-described variations, treatments, and modifications of tip (14) and/or cannula (12) may facilitate penetration of needle portion (350) into tissue, such as by reducing the force that is required to penetrate tissue when compared to other tips (14) and cannulas (12). Such reduced force to penetrate may be particularly useful in the context of probe (103) in the present example, as probe (103) is manipulated by a single hand of a user in some illustrative uses. In other words, biopsy device (101) may be grasped by a single hand of a user, and the user may insert needle portion (350) into tissue by using the single hand grasping biopsy device (101). Alternatively, biopsy device (101) may be used in a variety of other ways.

While the above-described variations, treatments, and modifications of tip (14) and/or cannula (12) are described in the context of biopsy device (101) of the present example, it should be understood that any of the above-described variations, treatments, and modifications of tip (14) and/or cannula (12) may be readily incorporated into virtually any type of biopsy device. By way of example only, any of the above-described variations, treatments, and modifications of tip (14) and/or cannula (12) may be readily incorporated into any of the biopsy devices taught in U.S. Pub. No. 2008/0214955, entitled "Presentation of Biopsy Sample by Biopsy Device," published Sep. 4, 2008, the disclosure of which is incorporated by reference herein. As another merely illustrative example, any of the above-described variations, treatments, and modifications of tip (14) and/or cannula (12) may be readily incorporated into any of the biopsy devices taught in U.S. patent application Ser. No. 12/337,942, entitled "Biopsy Device with Central Thumbwheel," filed Dec. 18, 2008, the disclosure of which is incorporated by reference herein. As yet another merely illustrative example, any of the above-described variations, treatments, and modifications of tip (14) and/or cannula (12) may be readily incorporated into any of the biopsy devices taught in U.S. patent application Ser. No. 12/483,305, entitled "Tetherless Biopsy Device with Reusable Portion," filed Jun. 12, 2009. As yet another merely illustrative example, any of the above-described variations, treatments, and modifications of tip (14) and/or cannula (12) may be readily incorporated into any of the biopsy devices taught in any other U.S. patent, U.S. patent application Publication, and U.S. patent application that is cited herein. Various suitable ways in which any of the above-described variations, treatments, and modifications of tip (14) and/or cannula (12) may be incorporated into such biopsy devices will be apparent to those of ordinary skill in the art in view of the teachings herein. Similarly, various other types of biopsy devices or other devices into which any of the above-described variations, treatments, and modifications of tip (14) and/or cannula (12) may be incorporated will be apparent to those of ordinary skill in the art in view of the teachings herein.

E. Exemplary Needle Hub

As shown in FIGS. 3-5, a needle hub (358) is secured to outer cannula (12) of probe (103), and comprises a thumbwheel (62) and a sleeve portion (360) extending proximally from thumbwheel (62). Needle hub (358) of the present example is overmolded about a proximal portion of outer cannula (12), though needle hub (358) may be formed and/or secured relative to outer cannula (12) using any other suitable techniques (e.g., set screws, etc.). Furthermore, while needle hub (358) of the present example is formed of a plastic material, any other suitable material or combination of materials may be used.

Needle hub (358) of the present example includes an interior portion that is in fluid communication with vacuum lumen (32) of outer cannula (12). Needle hub (358) may further be in fluid communication with manifold (359) that is in further communication with tube (402). Tube (402) and manifold (359) may thus provide fluids (e.g., vacuum, atmospheric air, saline, pressurized air, etc.) to vacuum lumen (32) of cannula (12). Suitable ways in which these components may be configured and operable are disclosed in U.S. Pub. No. 2008/0214955, entitled "Presentation of Biopsy Sample by Biopsy Device," published Sep. 4, 2008, the disclosure of which is incorporated by reference herein. Of course, any other suitable components, structures, or configurations may be used.

Thumbwheel (62) is operable to rotate outer cannula (12) about its longitudinal axis, relative to cover member (354) and base member (356). For instance, thumbwheel (62) may be used to orient aperture (16) to a number of desired orientations about the longitudinal axis defined by outer cannula (12). Such multiple orientations may be desirable, by way of example only, to obtain a plurality of tissue samples from a biopsy site, without requiring the needle portion (10) to be removed from the patient during the acquisition of such a plurality of tissue samples. An illustrative example of such rotation and acquisition of multiple tissue samples is disclosed in U.S. Pat. No. 5,526,822, the disclosure of which is incorporated by reference herein. Other ways in which multiple tissue samples may be obtained at various locations will be apparent to those of ordinary skill in the art in view of the teachings herein. For instance, rotation of outer cannula (12) may be motorized or automated. As another non-exhaustive example, an entire biopsy device (101) may be rotated during acquisition of tissue samples, without necessarily removing biopsy device (101) from the patient during such rotation and tissue sample acquisition, to obtain tissue samples from various orientations about the longitudinal axis defined by outer cannula (12).

F. Exemplary Tissue Sample Holder

In the present example, a tissue sample holder (368) is provided at the end of body portion (352) of probe (103). Tissue sample holder (368) comprises a cup (142), a rotatable manifold (not shown) contained within cup (142), and a plurality of removable sample trays (not shown) with a plurality of tissue sample chambers (not shown) positioned about the exterior of the rotatable manifold. Each tissue sample chamber is configured to separately hold a tissue sample communicated proximally through cutter lumen (52), such that tissue sample holder (368) may separately hold a plurality of tissue samples. In particular, the manifold is configured to rotate to selectively index each tissue sample chamber relative to cutter lumen (52). This rotation of the manifold is accomplished through rotation of gear (170), which meshes with a corresponding gear (not shown) of holster (302). The manifold is further configured to communicate a vacuum from tube (404) to cutter lumen (52), regardless of which tissue sample chamber is indexed relative to cutter lumen (52). Suitable components and structures for and methods of operating a tissue sample holder (368) are disclosed in U.S. Pub. No. 2008/0214955, entitled "Presentation of Biopsy Sample by Biopsy Device," published Sep. 4, 2008, the disclosure of which is incorporated by reference herein. Of course, any other suitable components, structures, or configurations may be used.

II. Exemplary Holster

As shown in FIGS. 1-2, holster (302) of the present example comprises a top housing member (304), through which a portion of gear (208) is exposed, and a bottom housing member (306). A plurality of hook members (305) extend from top housing member (304) for selectively securing probe (103) to holster (302), though other structures or techniques may be used. Holster (302) of the present example is thus configured to be coupled with a biopsy probe (103), such as biopsy probe (103) described above, to provide a biopsy device (101). In addition, holster (302) is configured to be handheld, such that biopsy device (101) may be manipulated and operated by a single hand of a user (e.g., using ultrasound guidance, etc.). However, it will be appreciated in view of the disclosure herein that holster (302) may be used in a variety of other settings and combinations.

Holster (302) of this example further comprises a cutter drive mechanism (not shown) and a tissue holder rotation mechanism (not shown). The cutter drive mechanism is operable to rotate gear (208), which in turn rotates gear (108) of probe (103) to provide simultaneous rotation and translation of cutter (50) relative to cannula (12). The tissue holder rotation mechanism is operable to rotate an exposed gear (not shown) of holster (302), which meshes with gear (170) of probe (103) to provide rotation of the manifold of tissue sample holder (368) to successively index tissue sample chambers to cutter lumen (52). Suitable components and structures that may be used to provide a cutter drive mechanism and a tissue holder rotation mechanism are disclosed in U.S. Pub. No. 2008/0214955, entitled "Presentation of Biopsy Sample by Biopsy Device," published Sep. 4, 2008, the disclosure of which is incorporated by reference herein. Of course, any other suitable components, structures, or configurations may be used. Alternatively, either or both of a cutter drive mechanism or a tissue holder rotation mechanism may simply be omitted altogether.

Holster (302) may also include a user interface that permits a user to enter commands to operate at least a portion of biopsy device (101). Suitable user interfaces that may be so incorporated into holster (302) are disclosed in U.S. Pub. No. 2008/0214955, entitled "Presentation of Biopsy Sample by Biopsy Device," published Sep. 4, 2008, the disclosure of which is incorporated by reference herein. Of course, any other suitable components, structures, or configurations may be used. Alternatively, holster (302) may simply lack a user interface altogether.

III. Other Exemplary Components and Variations

Biopsy device (101) may be coupled with a vacuum control module (not shown) that is operable to provide fluids (e.g., vacuum, atmospheric air, saline, pressurized air, etc.), power, and/or commands to biopsy device (101). For instance, such a vacuum control module may be coupled with a cable (not shown) that is also coupled with holster (302), to provide power and/or commands to drive the cutter drive mechanism, to selectively provide power and/or commands the tissue holder rotation mechanism, and/or to provide other functionality. Such a vacuum control module may also be coupled with tubes (402, 404), to selectively provide fluids (e.g., a vacuum) to cutter lumen (52) via the manifold of tissue sample holder (368) and/or to provide fluids (e.g., vacuum, atmospheric air, saline, pressurized air, etc.) to vacuum lumen (32) of cannula (12) via manifold (359) and needle hub (358). Such a vacuum control module may also include a user interface that permits a user to enter commands to operate at least a portion of biopsy device (101). Suitable examples of such a vacuum control module are disclosed in U.S. Pub. No. 2008/0214955, entitled "Presentation of Biopsy Sample by Biopsy Device," published Sep. 4, 2008, the disclosure of which is incorporated by reference herein. Of course, any other suitable components, structures, or configurations may be used.

While biopsy device (101) has been described herein as being usable in a handheld fashion and using ultrasound guidance, it should be understood that biopsy device (101) may be used in a variety of other ways and in a variety of other settings. By way of example only, biopsy device (101) may be used under stereotactic guidance, MRI guidance, PEM guidance, BSGI guidance, or otherwise. Biopsy device (101) may also be mounted to a table, pedestal, cradle, or other type of fixture instead of being handheld. Other suitable settings in which biopsy device (101) may be used, as well as other suitable ways in which biopsy device may be held and/or otherwise used, will be apparent to those of ordinary skill in the art in view of the teachings herein.

Embodiments of the present invention have application in conventional endoscopic and open surgical instrumentation as well as application in robotic-assisted surgery.

Embodiments of the devices disclosed herein can be designed to be disposed of after a single use, or they can be designed to be used multiple times. Embodiments may, in either or both cases, be reconditioned for reuse after at least one use. Reconditioning may include any combination of the steps of disassembly of the device, followed by cleaning or replacement of particular pieces, and subsequent reassembly. In particular, embodiments of the device may be disassembled, and any number of the particular pieces or parts of the device may be selectively replaced or removed in any combination. Upon cleaning and/or replacement of particular parts, embodiments of the device may be reassembled for subsequent use either at a reconditioning facility, or by a surgical team immediately prior to a surgical procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, embodiments described herein may be processed before surgery. First, a new or used instrument may be obtained and if necessary cleaned. The instrument may then be sterilized. In one sterilization technique, the instrument is placed in a closed a sealed container, such as a plastic or TYVEK bag. The container and instrument may then be placed in a field of radiation that can penetrate the container, such as gamma radiation, x-rays, or high-energy electrons. The radiation may kill bacteria on the instrument and in the container. The sterilized instrument may then be stored in the sterile container. The sealed container may keep the instrument sterile until it is opened in a medical facility. A device may also be sterilized using any other technique known in the art, including but not limited to beta or gamma radiation, ethylene oxide, or steam.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometrics, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

What is claimed is:

1. A biopsy probe, wherein the biopsy probe comprises:
   (a) a body portion;
   (b) a cannula extending distally from the body portion, wherein the cannula has a distal end, wherein the cannula defines at least one lumen, wherein the cannula comprises a lateral tissue receiving port configured to receive tissue, wherein the lateral tissue receiving port is proximal to the distal end of the cannula;
   (c) a tip extending distally from the cannula, wherein the tip comprises a sharp upper edge and a sharp lower edge, wherein the upper edge and the lower edge each define a respective proximal end, wherein the upper edge and the lower edge are positioned relative to each other to define a blade, wherein the lower edge extends proximally relative to the upper edge such that the proximal end of the lower edge is proximal to the proximal end of the upper edge; and
   (d) a cutter configured to translate relative to the cannula, wherein the cutter is configured to sever tissue received by the lateral tissue receiving port.

2. The biopsy probe of claim 1, wherein the cannula comprises a first lumen and a second lumen.

3. The biopsy probe of claim 2, wherein the cutter translates within the first lumen.

4. The biopsy probe of claim 3, the first lumen extending distally to a longitudinal position distal to a distal end of the second lumen.

5. The biopsy probe of claim 1, wherein the lateral tissue receiving port is defined in part by a proximal edge and a distal edge.

6. The biopsy probe of claim 5, the sharp upper edge extending proximally to a longitudinal position distal of the distal edge of the lateral tissue receiving port.

7. The biopsy probe of claim 5, the sharp lower edge extending proximally to a longitudinal position proximal of the distal edge of the lateral tissue receiving port and distal of the proximal edge of the lateral tissue receiving port.

8. The biopsy probe of claim 1, wherein the cannula defines a longitudinal axis, wherein the sharp upper edge is configured to extend proximally at a first acute angle relative to the longitudinal axis, wherein the sharp lower edge is configured to extend proximally at a second acute angle relative to the longitudinal axis, wherein the first acute angle is greater than the second acute angle.

9. The biopsy probe of claim 1, wherein the distal end of the cannula comprises a tissue stop extending proximally within the lumen of the cannula.

10. The biopsy probe of claim 9, the sharp upper edge extending proximally to a longitudinal position distal of the tissue stop.

11. The biopsy probe of claim 9, the sharp lower edge extending proximally to a longitudinal position proximal of the tissue stop.

12. The biopsy probe of claim 1, wherein a length of the sharp upper edge and a length of the sharp lower edge define an incision length.

13. The biopsy probe of claim 12, wherein the incision length is greater than or equal to an outer perimeter length of the cannula.

14. The biopsy probe of claim 1, wherein the cannula is rotatable relative to the body portion.

15. The biopsy probe of claim 1 further comprising a tissue sample holder configured to receive tissue samples severed by the cutter.

16. The biopsy probe of claim 15, wherein the tissue sample holder is removably supported by the body portion.

17. The biopsy probe of claim 16, wherein the tissue sample holder is rotatable relative to the body portion.

18. A biopsy probe, wherein the biopsy probe comprises:
(a) a body portion;
(b) a cannula extending distally from the body portion, wherein the cannula has a distal end, wherein the cannula defines at least one lumen, wherein the cannula comprises a lateral tissue receiving port configured to receive tissue, wherein the lateral tissue receiving port is proximal to the distal end of the cannula;
(c) a tip extending distally from the cannula, wherein the tip comprises a sharp upper edge having a first length and a sharp lower edge having a second length, wherein the first length and the second length define an incision length, wherein the incision length is greater than or equal to an outer perimeter length of the cannula, wherein the outer perimeter length is defined by the length of an outer perimeter of the cannula; and
(d) a cutter configured to translate relative to the cannula, wherein the cutter is configured to sever tissue received by the lateral tissue receiving port.

19. A surgical instrument for use in a breast biopsy procedure, wherein the surgical instrument comprises:
(a) a body portion;
(b) a cannula extending distally from the body portion, wherein the cannula has a distal end, wherein the cannula defines a longitudinal axis; and
(c) a tip extending distally from the cannula, wherein the tip comprises a sharp upper edge and a sharp lower edge, wherein the sharp upper edge is configured to extend proximally at a first acute angle relative to the longitudinal axis, wherein the sharp lower edge is configured to extend proximally at a second acute angle relative to the longitudinal axis, wherein the first acute angle is greater than the second acute angle.

* * * * *